(12) United States Patent
Holmqvist

(10) Patent No.: US 10,792,437 B2
(45) Date of Patent: Oct. 6, 2020

(54) SAFETY MECHANISM FOR A PUSH-OFF CAP OF A MEDICAMENT DELIVERY DEVICE

(71) Applicant: SHL MEDICAL AG, Zug (CH)

(72) Inventor: Anders Holmqvist, Värmdo (SE)

(73) Assignee: SHL MEDICAL AG, Zug (CH)

( * ) Notice: Subject to any disclaimer, the term of this patent is extended or adjusted under 35 U.S.C. 154(b) by 153 days.

(21) Appl. No.: 16/312,223

(22) PCT Filed: May 29, 2017

(86) PCT No.: PCT/EP2017/062847
§ 371 (c)(1),
(2) Date: Dec. 20, 2018

(87) PCT Pub. No.: WO2017/220287
PCT Pub. Date: Dec. 28, 2017

(65) Prior Publication Data
US 2019/0255256 A1    Aug. 22, 2019

(30) Foreign Application Priority Data
Jun. 21, 2016 (SE) ...................... 1650883

(51) Int. Cl.
*A61M 5/32* (2006.01)
*A61M 5/315* (2006.01)

(52) U.S. Cl.
CPC ...... *A61M 5/3204* (2013.01); *A61M 5/31576* (2013.01); *A61M 5/3202* (2013.01); *A61M 5/3213* (2013.01); *A61M 5/3287* (2013.01)

(58) Field of Classification Search
CPC .............. A61M 5/3204; A61M 5/3202; A61M 5/3213; A61M 5/3216; A61M 5/1626;
(Continued)

(56) References Cited

U.S. PATENT DOCUMENTS 10,159,806 B2   12/2018   Bjork et al.
10,166,336 B2    1/2019   Lumme et al.
(Continued)

FOREIGN PATENT DOCUMENTS

EP    2902063 A1    8/2015
GB    2436593 A    12/2007
(Continued)

OTHER PUBLICATIONS

Office Action issued in Swedish Patent Application No. 1650883-0 dated Jan. 11, 2017.
(Continued)

*Primary Examiner* — Kami A Bosworth
*Assistant Examiner* — Antarius S Daniel
(74) *Attorney, Agent, or Firm* — McDonnell Boehnen Hulbert & Berghoff LLP

(57) ABSTRACT

The present disclosure relates to a safety mechanism (5) for a push-off cap of a medicament delivery device. The safety mechanism (5) includes a cap (9) and an actuator assembly (11). The cap (9) has a through-opening (9b) and is configured to be mounted to the proximal end of a medicament delivery device. The actuator assembly (11) is configured to be received by the cap (9), and extend proximally from the cap (9). The actuator assembly (11) is linearly displaceable relative to the cap (9), from a first position in which the actuator assembly (11), to a second position in which the actuator assembly (11) is displaced in the distal direction and received further by the cap relative to the first position. The actuator assembly (11) includes a guide structure configured to guide linear displacement of the actuator assembly (11) relative to the cap (9), a proximal top member (11c) and a lock structure (11d). The proximal top member (11c) is pivotally arranged relative to the guide structure (11a), between a first pivot position and a second pivot position.
(Continued)

The lock structure (11d) extends distally, from a distal surface of the proximal top member (11c), from the proximal top member to the proximal end surface of the cap. By pivoting the proximal top member (11c) relative to the guide structure (11a), the lock structure (11d) which is pivotally fixed relative to the proximal top member, will also be pivoted. The proximal top member (11c) is pivotable from the first pivot position in which the lock structure (11d) is configured to be bear against the proximal end surface (9a) of the cap (9) to the second pivot position, in which the lock structure (11d) aligns with the through-opening (9b) of the cap (9).

13 Claims, 6 Drawing Sheets

(58) Field of Classification Search
CPC ...... A61M 5/150534; A61M 5/150587; A61M 5/150709; A61M 5/150725; A61M 2005/3117; A61M 2005/208; A61M 2005/3206; A61M 2005/3215; A61M 2005/312; A61M 2005/3118; A61M 39/20; A61M 2039/205; B43K 23/08; B65D 41/0485; B65D 41/02; B65D 2543/00888

See application file for complete search history.

(56) References Cited

U.S. PATENT DOCUMENTS

| | | | |
|---|---|---|---|
| 2013/0068716 A1* | 3/2013 | Laperriere | B65D 41/02 215/316 |
| 2015/0051553 A1 | 2/2015 | Bjork et al. | |
| 2016/0331908 A1* | 11/2016 | Bode | A61M 5/3204 |

FOREIGN PATENT DOCUMENTS

| | | |
|---|---|---|
| TW | 201315499 A1 | 4/2013 |
| TW | 201400158 A | 1/2014 |
| WO | 2007077463 A1 | 7/2007 |
| WO | 2013135566 A2 | 9/2013 |
| WO | 2016012278 A1 | 1/2016 |

OTHER PUBLICATIONS

Search Report issued in Taiwanese Patent Application No. 106119132 dated Mar. 7, 2018.

* cited by examiner

SAFETY MECHANISM FOR A PUSH-OFF CAP OF A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2017/062847 filed May 29, 2017 which claims priority to Swedish Patent Application No. 1650883-0 filed Jun. 21, 2016. The entire disclosure contents of these applications are hereby incorporated by reference into the present application.

TECHNICAL FIELD

The present disclosure generally relates to medical devices. In particular, it relates to a push-off cap for a medicament delivery device.

BACKGROUND

Medicament delivery devices such as injectors typically have a body comprising a medicament container and a medicament delivery member such as a needle. The proximal end of the body, i.e. that end which faces the administration site during medicament delivery is normally provided with a cap before the commencement of medicament administration. The cap is fitted for the purpose of mechanical protection of the internal components of the medicament delivery device and to provide a sterile environment for the medicament delivery member.

In order to ensure that the cap is maintained in its intended protective position until use of the medicament delivery device, the cap is attached to the body in such a way that it requires a certain non-negligible force to be removed from the body. Removal of the cap is typically performed by the user prior to medicament administration. Some users such as children, elderly, and people with arthritis or rheumatic disorder may have poor dexterity and may therefore find it difficult to remove the cap.

An example of a protective cap is disclosed in WO 2013/135566, which discloses a medicament delivery device that comprises a housing configured to receive a medicament container having a delivery member and a shield, and a protective cap assembly including a protective cap. The protective cap comprises connecting means for connecting to the shield of the medicament container such that removal of the protective cap from the housing causes removal of the shield from the medicament container. The protective cap 30o assembly comprises first disconnecting means configured to interact with corresponding second disconnecting means of the housing and of the protective cap such that activation of the first disconnecting means of the protective cap assembly causes the displacement of the protective cap relative to the housing. A user is thereby able to remove the cap from the device by pushing the cap towards a solid surface. This manoeuvre can for example be performed with only one hand, and allows users with poor dexterity to remove the cap in a simple manner.

There are certain requirements, so-called drop-test requirements, which should be fulfilled by medicament delivery devices. These essentially state that a medicament delivery device should be able to be dropped from a certain height onto its proximal end, distal end, and onto the side without any mechanical damage or activation of the device. The protective cap assembly of the device disclosed WO 2013/135566 could potentially be triggered in case of a drop test.

SUMMARY

In view of the above, a general object of the present disclosure is to provide a safety mechanism for a push-off cap of a medicament delivery device which solves or at least mitigates the problems of the prior art.

There is hence according to a first aspect of the present disclosure provided a safety mechanism for a push-off cap of a medicament delivery device, wherein the safety mechanism comprises: a cap having a proximal end surface provided with a through-opening, which cap is configured to be mounted to a proximal end of a medicament delivery device, and an actuator assembly configured to be received by and extend proximally from the cap, wherein the actuator assembly is linearly displaceable relative to the cap from a first position in which the actuator assembly extends proximally from the cap to a second position in which the actuator assembly is displaced distally and received further by the cap relative to the first position, wherein the actuator assembly has a guide structure configured to guide linear movement of the actuator assembly from the first position to the second position, and a lock assembly having: a proximal top member that is pivotable relative to the guide structure, and a lock structure extending distally from the proximal top member to the proximal end surface of the cap, wherein the lock structure is pivotally fixed relative to the proximal top member, and wherein the lock structure is configured to be received by the through-opening of the cap, wherein the proximal top member is pivotable from a first pivot position relative to the guide structure, in which the lock structure is configured to bear against the proximal end surface of the cap to prevent the actuator assembly from being displaced from the first position to the second position, to a second pivot position relative to the guide structure, in which the lock structure is configured to align with the through-opening, allowing the actuator assembly to be displaced from the first position to the second position thereby enabling releasing of the cap from a medicament delivery device.

The safety mechanism provides the push-off cap with release protection, enabling releasing of the cap when the cap is pressed against a solid surface at a slight angle. It furthermore allows the user to remove the cap with a single-push operation. A medicament delivery device provided with a push-off cap provided with this safety mechanism fulfils the requirements of a drop-test while facilitating cap removal for users with poor dexterity.

According to one embodiment the lock structure extends distally from the proximal top member in an inclined manner relative to the central longitudinal axis of the safety mechanism, in the first pivot position. The lock structure will thus not be able to be received by the through-opening of the cap in this inclined state, especially since the through-opening is dimensioned to receive the lock structure only when it extends parallel with the longitudinal axis of the safety mechanism.

According to one embodiment the proximal top member is configured to be arranged parallel with the proximal end surface of the cap in the first pivot position. This is the manner in which the proximal top member would be oriented in a vertical drop test, and it ensures that the lock structure is oriented in an inclined manner in which it cannot be received by the through-opening of the cap.

According to one embodiment the proximal top member is configured to be angled relative to the proximal end surface of the cap in the second pivot position. The locking structure thereby obtains a parallel or essentially parallel orientation relative to the central longitudinal axis of the safety mechanism, causing it to be receivable by the through-opening in the event that the actuator assembly is displaced from the first position to the second position.

According to one embodiment the proximal top member is hingedly connected to a proximal end of the guide structure.

According to one embodiment the guide structure forms a portion of a cylinder.

According to one embodiment the lock structure forms a portion of a cylinder and is concentrically arranged with the guide structure.

According to one embodiment the lock structure is arranged radially inwards relative to the guide structure.

According to one embodiment the guide structure is configured to enable releasing of the cap from a medicament delivery device when the actuator assembly is displaced from the first position towards the second position.

According to one embodiment the proximal top member is generally disc-shaped.

According to one embodiment the guide structure is configured to extend through the through-opening of the proximal end surface of the cap, thereby guiding linear displacement of the actuator assembly.

There is according to a second aspect of the present disclosure provided a medicament delivery device comprising: a housing, a safety mechanism according to the first aspect, and a release mechanism, wherein the actuator assembly is configured to actuate the release mechanism when linearly displaced from the first position to the second position to thereby remove the cap.

According to one embodiment the outer surface of the housing has a proximal end portion provided with a fulcrum structure, and the release mechanism includes a lever configured to engage with the cap, wherein the guide structure is configured to tilt the lever about the fulcrum structure when the actuator assembly is displaced from the first position to the second position, thereby causing removal of the cap.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

Figure 1:
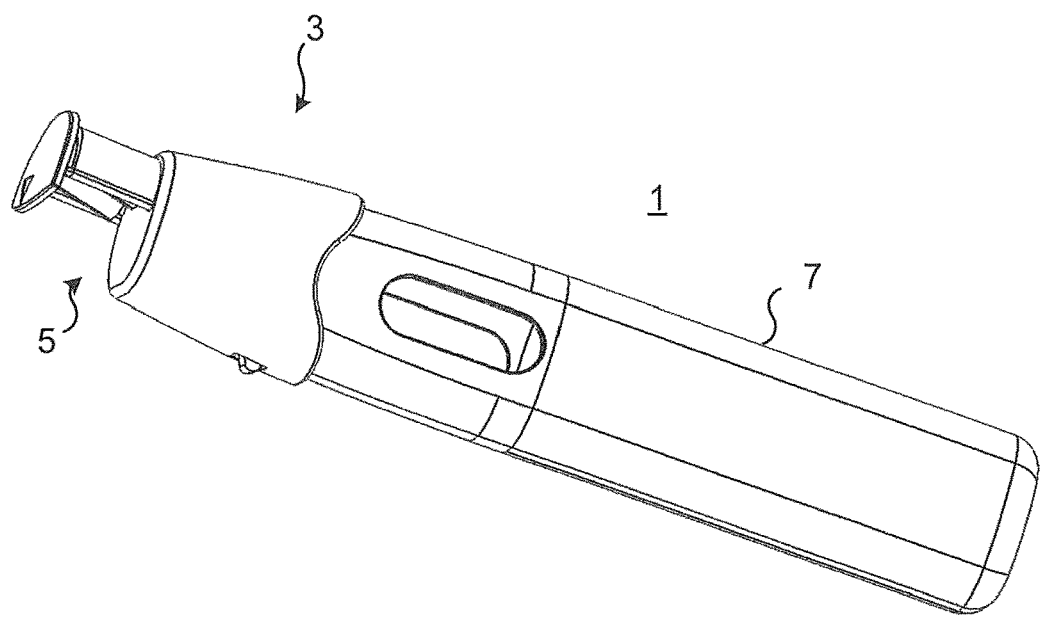
FIG. 1 is a perspective view of an example of a medicament delivery device comprising a push-off cap having a safety mechanism.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with a safety mechanism, refers to that end of the safety mechanism which when fitted to a medicament delivery device forms the proximal end of the thereby obtained medicament delivery device. The proximal end of the medicament delivery device is that end which is to be pointed towards the site of injection during medicament expulsion. The same considerations also apply when referring to any component of the safety mechanism. The "distal end" is the opposite end relative to the proximal end. With "proximal direction" and, equivalently, "proximally" is meant a direction from the distal end towards the proximal end, along the central axis of the safety mechanism. With "distal direction" or "distally" is meant the opposite direction to "proximal direction".

The present disclosure relates to a safety mechanism for a push-off cap of a medicament delivery device. The safety mechanism includes a cap and an actuator assembly. The cap has a through-opening and is configured to be mounted to the proximal end of a medicament delivery device. The cap may be attached to the medicament delivery device by means of friction. The actuator assembly is configured to be received by the cap, and extend proximally from the cap. In particular, the actuator assembly is linearly displaceable relative to the cap, from a first position in which the actuator assembly extends proximally from the cap, to a second position in which the actuator assembly is displaced in the distal direction and received further by the cap relative to the first position. The actuator assembly includes a guide structure configured to guide linear displacement of the actuator assembly relative to the cap, and a lock assembly having a proximal top member and a lock structure. The proximal top member is pivotally arranged relative to the guide structure, between a first pivot position and a second pivot position. In particular, the proximal top member is configured to be pivotally connected to the guide structure. The lock structure extends distally, from a distal surface of the proximal top member, from the proximal top member towards the proximal end surface of the cap. The lock structure is arranged in a pivotally fixed manner relative to the proximal top member.

By pivoting the lock assembly, in particular the proximal top member relative to the guide structure, the lock structure which is pivotally fixed relative to the proximal top member, will also be pivoted. In particular, the proximal top member is pivotable from the first pivot position in which the lock structure is configured to be bear against the proximal end surface of the cap, preventing the actuator assembly to be displaced to the second position, to the second pivot position, in which the lock structure is configured to align with the through-opening of the cap. Due to this alignment, the actuator assembly is able to be further received by the cap and thus to be displaced from the first position to the second position, thereby cooperating with a release mechanism, causing release of the cap from a medicament delivery device.

With reference to FIGS. 1-4, an example of a safety mechanism will now be described.

FIG. 1 shows an example of medicament delivery device 1. The exemplified medicament delivery device 1 comprises a push-off cap, of which one example is shown in FIG. 1. Push-off cap 3 comprises a safety mechanism 5, which in its default state prevents the push-off cap 3 from being released from its mounted position on the medicament delivery device 1 in the event that the push-off cap 3 is subjected to a distally directed linear force that only includes an axial component and no other force component.

The medicament delivery device 1 includes a housing 7, to which the push-off cap 3 may be mounted, and from which the push-off cap 3 may be released or removed.

Figure 2:
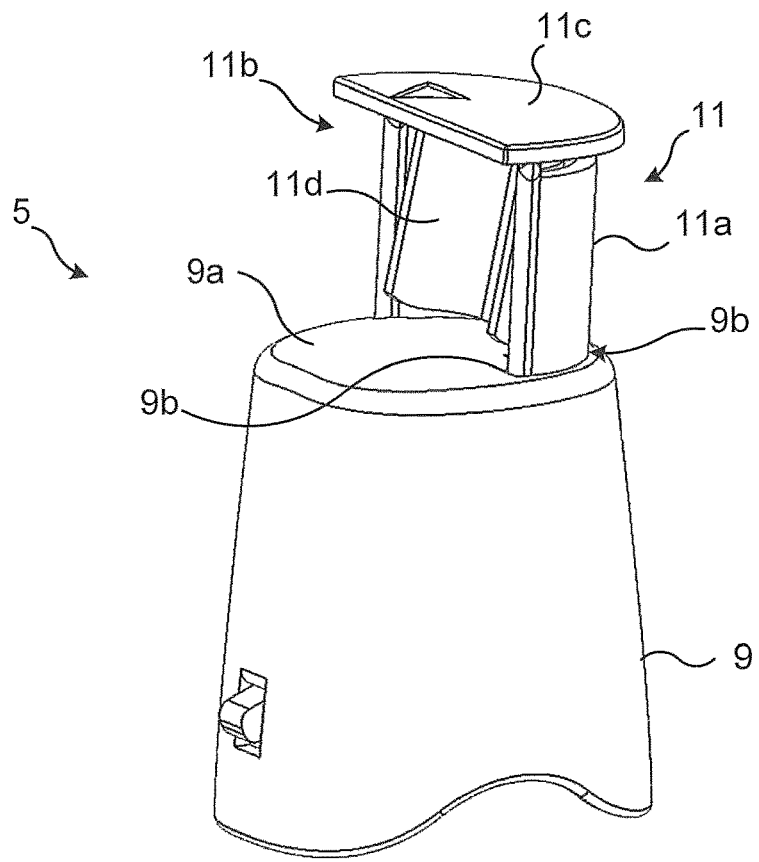
FIG. 2 is a perspective view of the safety mechanism in FIG. 1.

FIG. 2 shows a perspective view of the exemplified push-off cap 3, and in particular of the safety mechanism 5. The safety mechanism 5 has a cap 9, and an actuator assembly 11. The cap 9 has a proximal end surface 9a provided with a through-opening 9b configured to receive the actuator assembly 11. The actuator assembly 11 is configured to be linearly displaceable relative to the cap 9, in the axial direction of the cap 3, in particular between a first position in which the actuator assembly 11 extends proximally from the cap 9, and a second position, in which the actuator assembly 11 is displaced in the distal direction and further received by the cap 9 compared to the amount it is being received in the first position.

The push-off cap 3 has a release mechanism, not shown in FIG. 2, which is configured to cooperate with the actuator assembly 11. In particular, the release mechanism is configured to be manoeuvred by the actuator assembly 11 when it is displaced from the first position towards the second position, causing the push-off cap 3 to be released from the medicament delivery device 1.

The actuator assembly 11 includes a guide structure 11a configured to guide linear movement of the actuator assembly 11 from the first position to the second position. According to the present example, the guide structure 11a is configured to cooperate with the through-opening 9b, or the inner walls thereof, to guide linear motion of the actuator assembly 11 in a controlled manner.

The actuator assembly 11 furthermore includes a lock assembly 11b having a proximal top member 11c and a lock structure 11d. The proximal top member 11c is pivotally connected to the guide structure 11a, allowing the proximal top member 11c to pivot relative to the guide structure 11a between a first pivot position and a second pivot position. According to the present example, the proximal top member 11c is hingedly connected to the guide structure 11a.

The lock structure 11d is fixedly arranged relative to the proximal top member 11c. The lock structure 11d may be integrated with the proximal top member 11c, thus forming a single part lock assembly, or alternatively the lock structure 11d may be fixedly and immovably attached to the proximal top member 11c. The lock structure 11d is configured to extend generally in the distal direction from an underside, or distal end surface, of the proximal top member 11c, towards the proximal end surface 9a of the cap 9. Furthermore, the lock structure 11d has a straight or generally straight longitudinal extension along its entire longitudinal extension. The lock structure 11d is slightly inclined relative to a plane defined by the proximal top member 11c. In particular, an acute angle is formed between the lock structure 11d and the plane. In the first pivot position of the proximal top member 11b, the lock structure 11d defines a plane that intersects the central longitudinal axis of the cap 9 and thus also of the safety mechanism 5. In the first pivot position, the proximal top member 11c is generally arranged in parallel with the proximal end surface 9a of the cap 9. The lock structure 11d which in the first pivot position extends in an inclined manner relative to the central longitudinal axis will not be aligned with the through-opening 9b of the cap 9. The lock structure 11d will therefore bear against the proximal end surface 9a of the cap 9, in the event that the proximal top member 11c is pushed in the distal direction while being in the first pivot position. The actuator assembly 11 will thereby be prevented from displacement to obtain the second position.

In the second pivot position of the proximal top member 11b, the proximal top member 11b becomes angled relative to the proximal end surface 9a of the cap 9. The lock structure 11d is thus configured to align with the through-opening 9b of the cap 9, and to obtain an orientation parallel with or essentially parallel with the central longitudinal axis of the cap 9, allowing the lock structure 11d to be received by the through-opening 9b and enabling the actuator assembly 11 to be moved from the first position to the second position.

Figure 3:
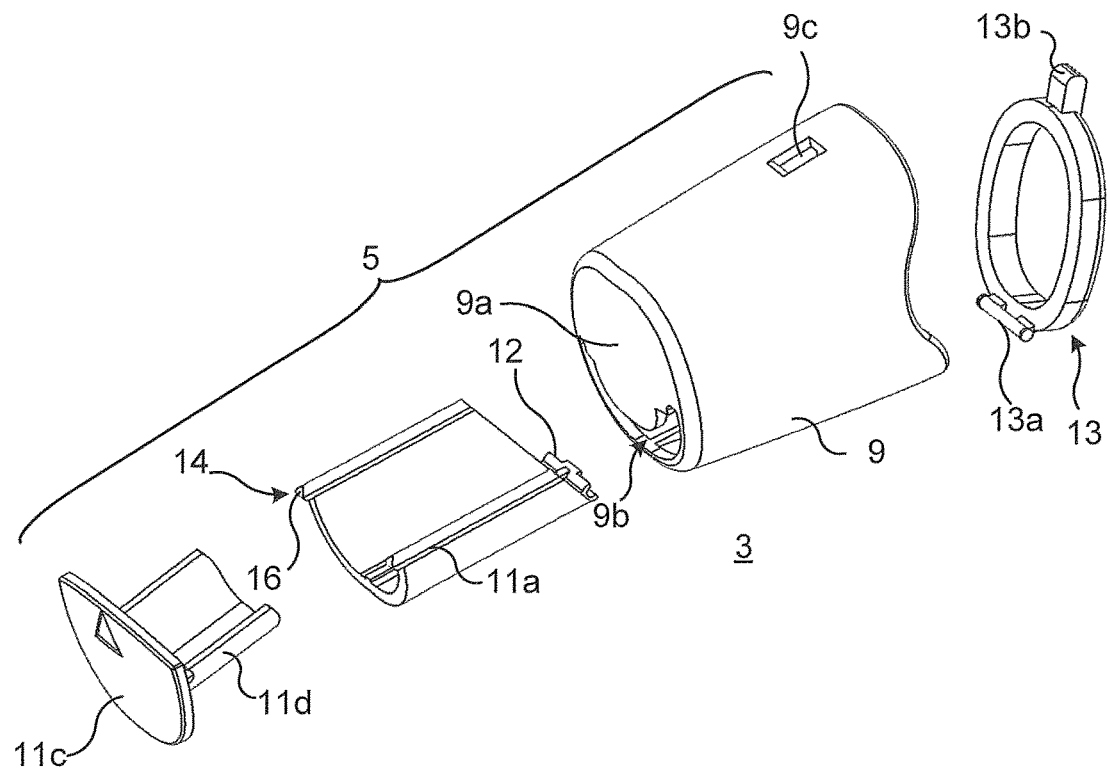
FIG. 3 is an exploded view of a push-off cap including the safety mechanism in FIG. 2.

Turning now to FIG. 3, an exploded view of the exemplified push-off cap 3 is shown. As can be seen, the guide structure 11a has a curved cross-sectional shape. The exemplified guide structure 11a has a shape that forms part of a cylinder, or is essentially U-shaped. The through-opening 9b of the exemplified cap 9 also has a curved shape, designed to be able to receive the guide structure 11a, but also the lock structure 11d when it is aligned with the through-opening 9b. The through-opening 9b is hence according to one variation configured to receive both the guide structure 11a and the lock structure 11d. According to the present example the lock structure 11d also has a curved cross-sectional shape. The exemplified lock structure 11d is essentially U-shaped, having a shape that forms part of a cylinder. The lock structure 11d is configured to be arranged concentrically with and radially inwards of the guide structure 11a.

Figure 4:
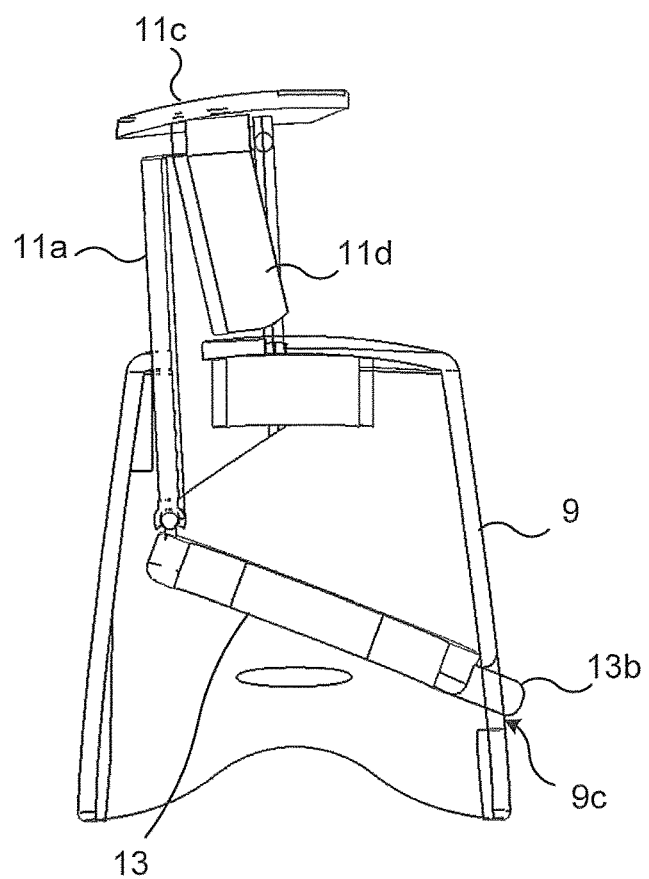
FIG. 4 is a longitudinal section of the push-off cap in FIG. 3.
Figure 5:
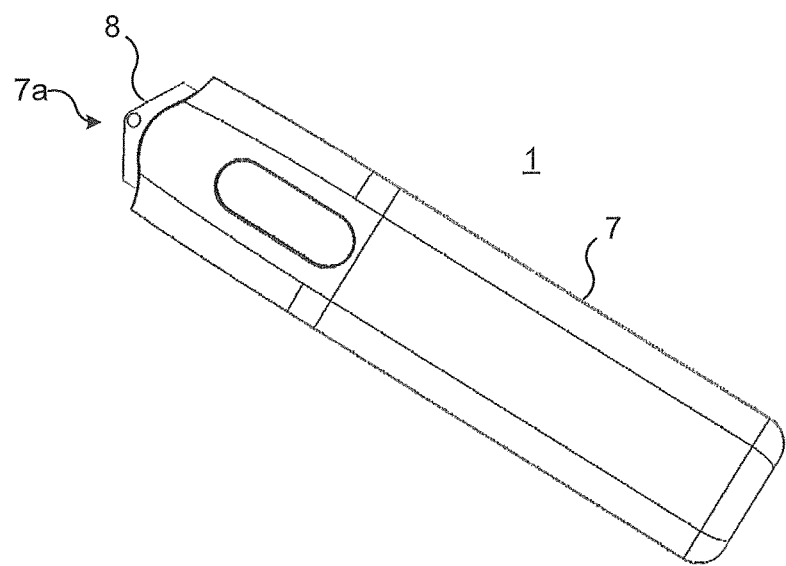
FIG. 5 is a side view of the medicament delivery device in FIG. 1 with the push-off cap removed.

The push-off cap 3 has a release mechanism which is configured to cooperate with the actuator assembly 11 and with the medicament delivery device 1, to cause the push-off cap 3 to be released from a medicament delivery device 1. The exemplified release mechanism includes a lever 13. The exemplified lever 13 is annular and pivotally connected to the guide structure 11a. In particular, the lever 13 is pivotally connected to a distal end of the guide structure 11a. According to the present example, the guide structure 11a has a hinge part 12, and the annular lever has a corresponding hinge part 13a which are configured to be connected in a hinged manner. The lever 13 has a radial protrusion 13b and the cap 9 has an inner surface provided with a recess 9c, in the present example a through-opening, configured to receive the radial protrusion 13, as shown in FIG. 4. The lever 13 is configured to be arranged inside the cap 9, and to cooperate with a proximal end of the housing 7 of the medicament delivery device 1.

The housing 7 has a proximal end portion 7a provided with a fulcrum structure 8. The guide structure 11a is configured to manoeuvre the lever 13 such that it tilts about the fulcrum structure 8 when the guide structure 11a is moved from the first position to the second position. The radial protrusion 13b is arranged in the recess 9c which are configured to act like a hinge. Tilting of the lever 13 causes the release of the cap 9 from the housing 7.

It should be noted that the release mechanism may be implemented in a number of different ways. WO 2013/135566, for example, discloses several examples of a release mechanism including a guide structure of the same type as guide structure 11a. One example according to WO 2013/135566 includes a release mechanism that comprises a guide member having a generally tubular shape, forming a first disconnecting means. The guide member is arranged to contact a proximal end surface of the housing with a distal end surface. The proximal end surface forms second disconnecting means. The guide member is arranged with longitudinally extending guides, which are arranged to fit in corresponding grooves on inner surfaces of the cap. With this arrangement, the guide member is rotationally locked to the cap and thereby to the housing. A proximally directed end surface of the guide member is arranged with a cut-out having an inclined first surface. The release mechanism further comprises a rotator having a generally tubular shape, which rotator is comprised in the first disconnecting means. The rotator has a diameter somewhat smaller than the guide member and arranged extending into the guide member. The rotator is arranged with a radially outwardly extending protrusion, which protrusion is designed to be in contact with the first inclined surface. The rotator is further arranged with a cut-out having an inclined second surface. A guide structure is arranged extending through an opening in a proximal end surface of the cap, where the opening has a shape corresponding to the shape of the guide structure. The guide structure may further be arranged with a radially extending protrusion on a side surface, which protrusion is designed to be in contact with the second inclined surface. The cap is further arranged with a distally directed end surface, forming second disconnecting means of the cap. When a user is to remove the cap for administering a dose of medicament, the medicament delivery device is gripped such that the proximal part of the device, including the cap, may be pressed against a solid surface. Thus, when the cap is pressed, the guide structure is forced in the distal direction into the cap. This linear movement causes the protrusion of the guide structure to act on the second inclined surface of the rotator. Due to the inclination of the second surface and the rotational lock of the guide structure, the rotator is forced to rotate. The rotation of the rotator causes its protrusion to act on the first inclined surface of the guide member. Due to the inclination of the first inclined surface and the rotational lock of the guide member, the rotator is moved in the proximal direction during rotation. The rotator is designed such that a proximal end surface thereof is in contact with the distally directed surface of the protective cap whereby a movement of the rotator in the proximal direction causes also the cap to be moved in the proximal direction against the friction force between the protective cap and the housing and the friction force between the needle shield and the injection needle.

Turning now to FIGS. 6a-8b the function of the safety mechanism 5 will now be described, as well as the release functionality of the push-off cap 3.

Figure 6A:
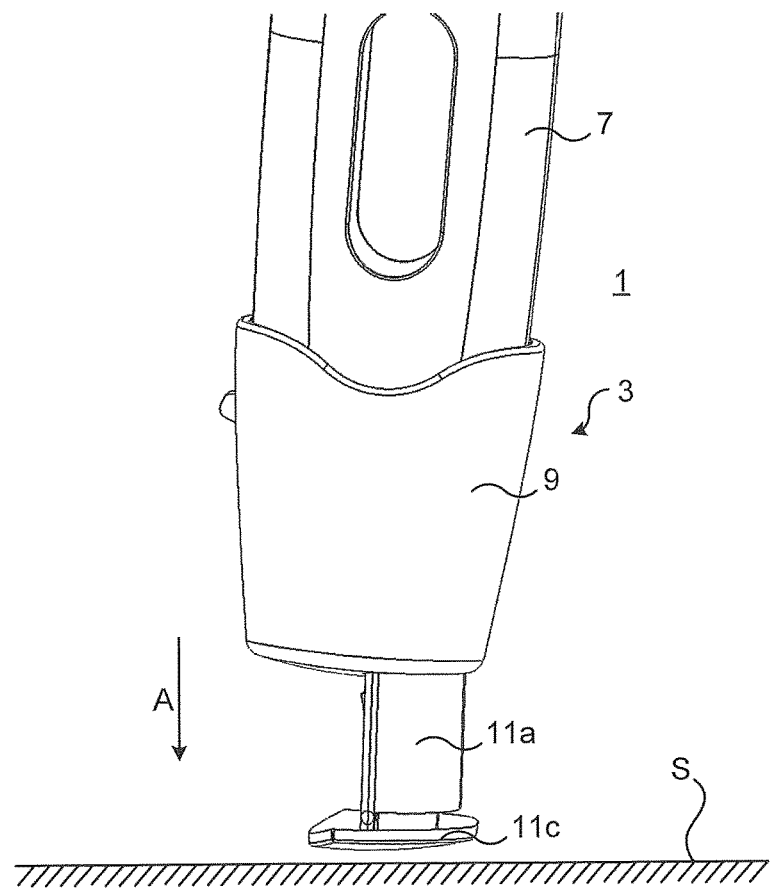
FIGS. 6a and 6b show a side views and a longitudinal section, respectively, of a medicament delivery device provided with a push-off cap including a safety mechanism prior to removal of the push-off cap.
Figure 6B:
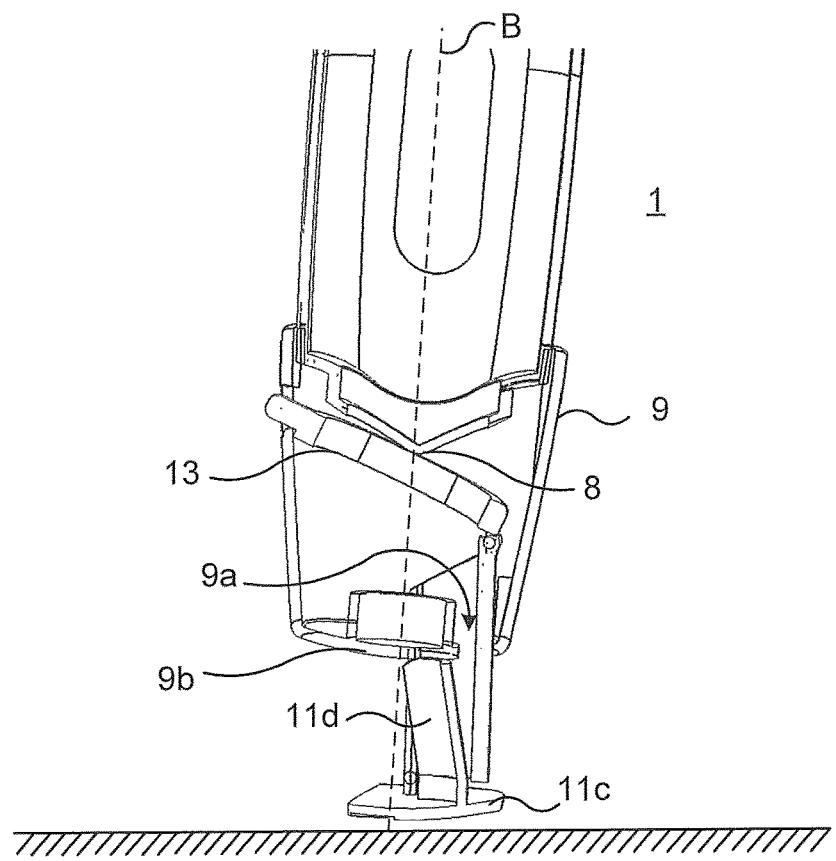

FIG. 6a shows a side view of the medicament delivery device 1 provided with the push-off cap 3, which is attached to the housing 7 by means of friction. The medicament delivery device 1 is moved by a user towards a solid surface S in the direction shown by arrow A. The actuator assembly 11 is in the first position and the proximal top member 11c is in the first pivot position. In FIG. 6b, which shows the same state of the safety mechanism as FIG. 6a, it can be seen that the lock structure 11d is inclined relative to the longitudinal axis B of the medicament delivery device 1. Hereto, the through-opening 9a is not able to receive the lock structure 11d, which in this case is not aligned with the through-opening 9a. Thus, when the medicament delivery device 1 is pushed towards the surface S, the actuator assembly 11 will be prevented from being moved from the first position to the second position because the lock structure 11d would be pressed against the proximal end surface 9a of the cap 9, thus acting as a stop.

Figure 7A:
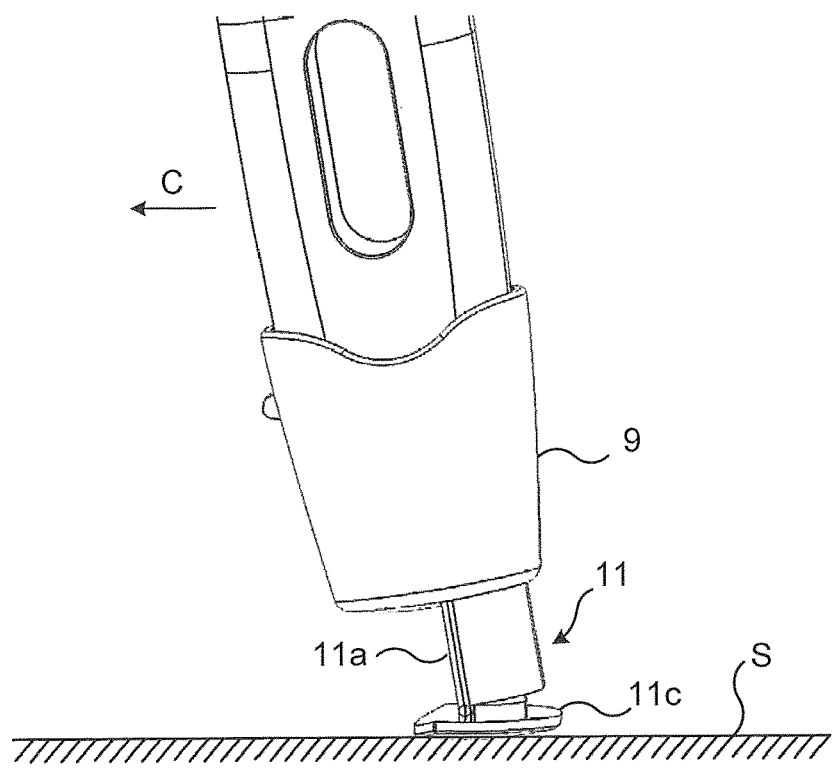
FIGS. 7a and 7b show a side view, and a longitudinal section, respectively, of a medicament delivery device provided with a push-off cap including a safety mechanism during activation of the push-off cap.
Figure 7B:
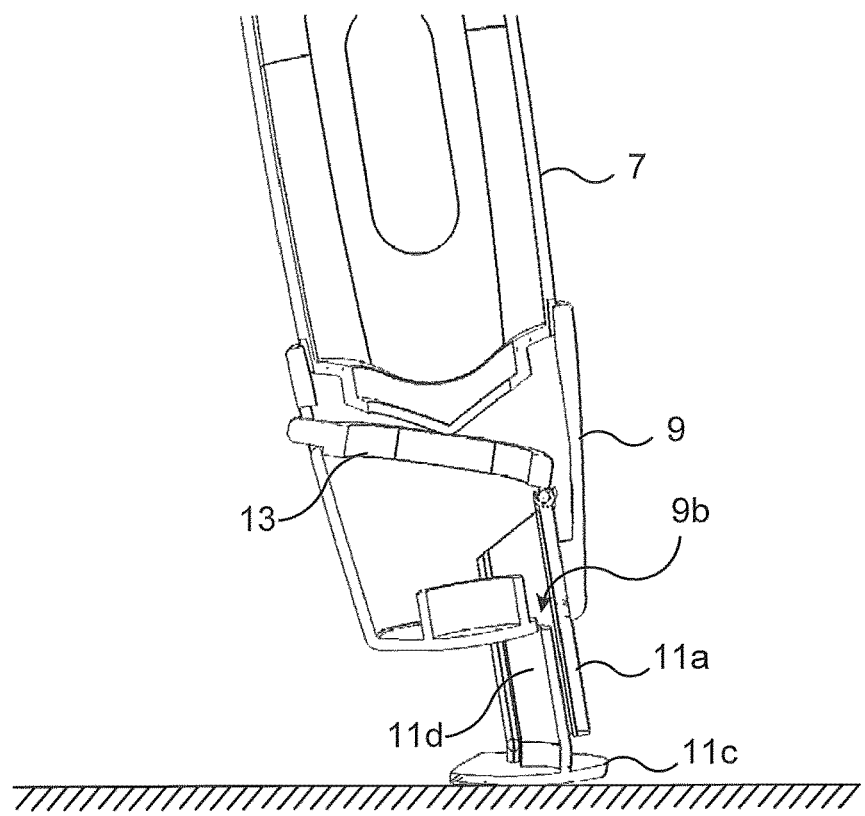

In the situation shown in FIG. 7a, the medicament delivery device 1 has attained contact with the surface S, and has furthermore been tilted to the left as shown by arrow C. This causes the guide structure 11a to be tilted or pivoted relative to the proximal top member 11c, and to obtain the second pivot position. The lock structure 11d is thereby aligned with the through-opening 9a of the cap 9. In FIG. 7b it can be seen that the lock structure 11d has not yet been pushed through the through-opening 9a, in particular it is still in the first position. The actuator assembly 11 has thus not yet manoeuvred the lever 13 and the cap 9 is still fully attached to the housing 7.

Figure 8A:
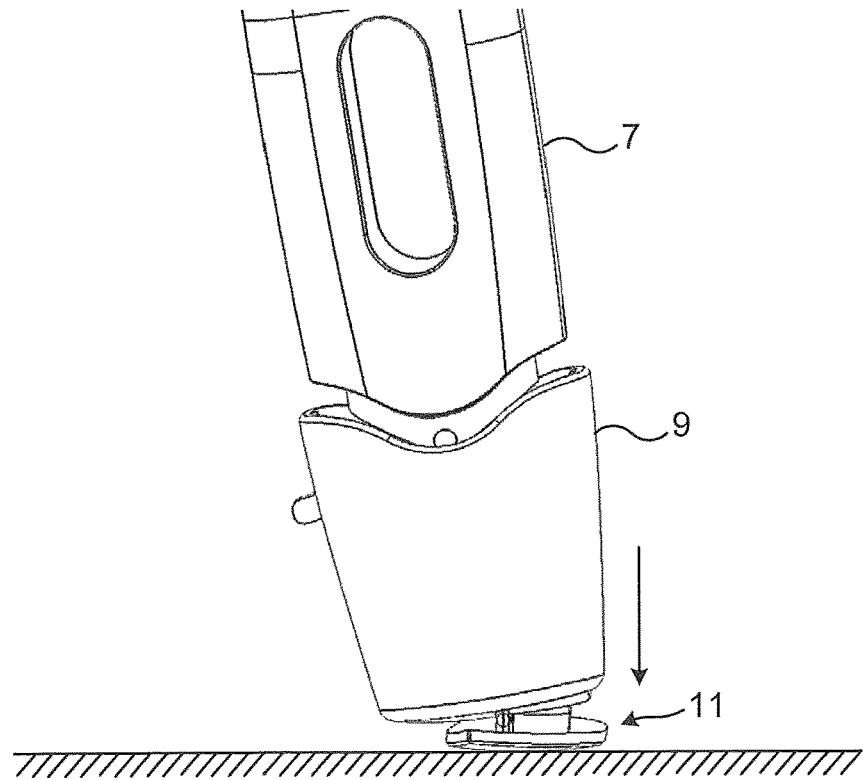
FIGS. 8a and 8b show a side view, and a longitudinal section, respectively, of a medicament delivery device provided with a push-off cap including a safety mechanism when the push-off cap has been released from the housing.
Figure 8B:
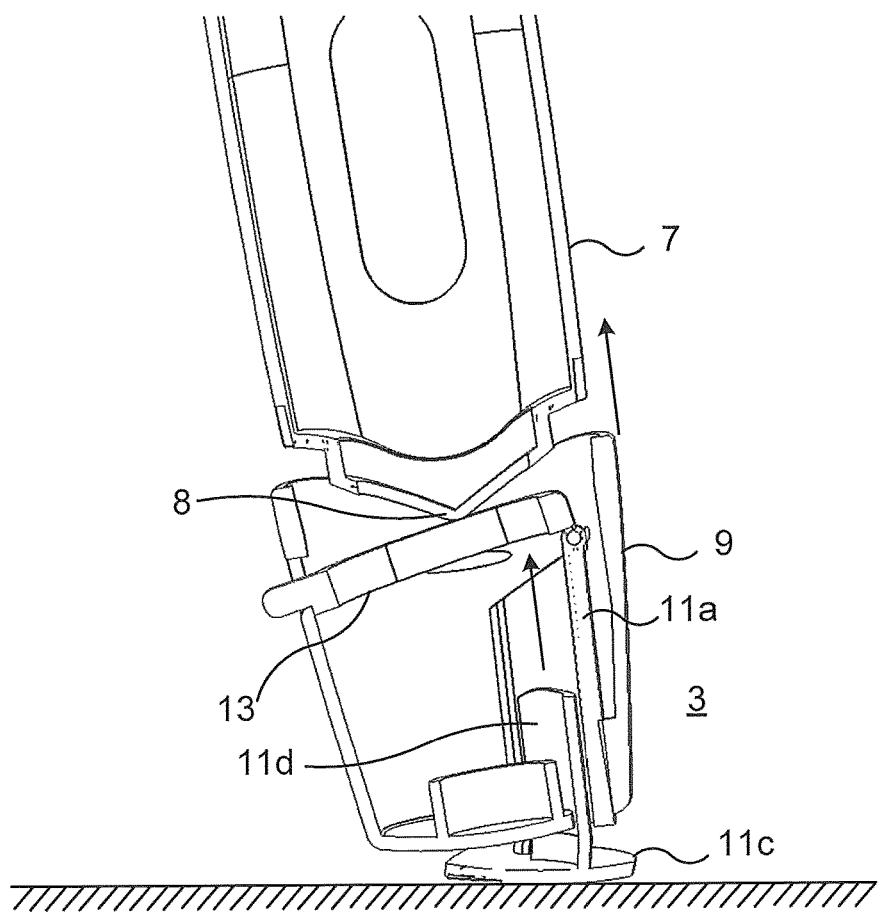

In FIG. 8a, the medicament delivery device 1 has been further pressed towards the surface S and the actuator assembly 11 has been pushed into the cap 9. The displacement of the actuator assembly 11 from the first position to the second position causes tilting of the lever 13 about the fulcrum structure 8 of the housing 7, causing the lever 13 to push the housing 7 away from the push-off cap 3, thereby releasing the push-off cap 3 from the housing 7.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A safety mechanism for a push-off cap of a medicament delivery device, wherein the safety mechanism comprises:
   a cap having a proximal end surface provided with a through-opening, wherein the cap is configured to be mounted to a proximal end of the medicament delivery device, and
   an actuator assembly configured to be received by and extend proximally from the cap, wherein the actuator assembly is linearly displaceable relative to the cap from a first position in which the actuator assembly extends proximally from the cap to a second position in which the actuator assembly is displaced distally and received further by the cap relative to the first position,
   wherein the actuator assembly has a guide structure configured to guide linear movement of the actuator assembly from the first position to the second position, and a lock assembly having:
      a proximal top member that is pivotable relative to the guide structure, and a lock structure extending distally from the proximal top member to the proximal end surface of the cap, wherein the lock structure is pivotally fixed relative to the proximal top member, and wherein the lock structure is configured to be received by the through-opening of the cap, wherein the proximal top member is pivotable from a first pivot position relative to the guide structure, in which the lock structure is configured to bear against the proximal end surface of the cap to prevent the actuator assembly from being displaced from the first position to the second position, to a second pivot position relative to the guide structure, in which the lock structure is configured to align with the through-opening, allowing the actuator assembly to be displaced from the first position to the second position thereby enabling releasing of the cap from the medicament delivery device.

2. The safety mechanism as claimed in claim 1, wherein the lock structure extends distally from the proximal top member in an inclined manner relative to a central longitudinal axis of the safety mechanism when the proximal top member is in the first pivot position.

3. The safety mechanism as claimed in claim 1, wherein the proximal top member is configured to be arranged parallel with the proximal end surface of the cap in the first pivot position.

4. The safety mechanism as claimed in claim 1, wherein the proximal top member is configured to be angled relative to the proximal end surface of the cap in the second pivot position.

5. The safety mechanism as claimed in claim 1, wherein the proximal top member is hingedly connected to a proximal end of the guide structure.

6. The safety mechanism as claimed in claim 1, wherein the guide structure forms a portion of a cylinder.

7. The safety mechanism as claimed in claim 6, wherein the lock structure forms a portion of a cylinder and is concentrically arranged with the guide structure.

8. The safety mechanism as claimed in claim 7, wherein the lock structure is arranged radially inwards relative to the guide structure.

9. The safety mechanism as claimed in claim 1, wherein the guide structure is configured to enable releasing of the cap from the medicament delivery device when the actuator assembly is displaced from the first position towards the second position.

10. The safety mechanism as claimed in claim 1, wherein the proximal top member is generally disc-shaped.

11. The safety mechanism as claimed in claim 1, wherein the guide structure is configured to extend through the through-opening of the proximal end surface of the cap, thereby guiding linear displacement of the actuator assembly.

12. A medicament delivery device comprising:
a housing,
a safety mechanism as claimed in claim 1, and
a release mechanism,
wherein the actuator assembly is configured to actuate the release mechanism when linearly displaced from the first position to the second position to thereby remove the cap.

13. The safety mechanism as claimed in claim 12, wherein an outer surface of the housing has a proximal end portion provided with a fulcrum structure, and the release mechanism includes a lever configured to engage with the cap, wherein the guide structure is configured to tilt the lever about the fulcrum structure when the actuator assembly is displaced from the first position to the second position, thereby causing removal of the cap.

* * * * *